United States Patent [19]

Fellingham et al.

[11] Patent Number: 4,950,244

[45] Date of Patent: Aug. 21, 1990

[54] PRESSURE SENSOR ASSEMBLY FOR DISPOSABLE PUMP CASSETTE

[75] Inventors: George H. Fellingham, San Jose; Michael Lawless, Boulder Creek, both of Calif.

[73] Assignee: Abbott Laboratories, Abbott Park, Ill.

[21] Appl. No.: 45,949

[22] Filed: May 1, 1987

[51] Int. Cl.⁵ .............................................. A61M 1/00
[52] U.S. Cl. ..................................... 604/118; 73/726; 128/675
[58] Field of Search ................. 604/118; 128/675, 748; 73/726, 730

[56] References Cited

U.S. PATENT DOCUMENTS

| | | | |
|---|---|---|---|
| 3,418,853 | 12/1968 | Curtis | 128/675 |
| 3,461,416 | 8/1969 | Kaufman | 73/726 |
| 3,698,249 | 10/1972 | Weaver | 73/726 |
| 3,722,264 | 3/1973 | Talmo et al. | 73/726 |
| 3,750,475 | 8/1973 | Weaver | 73/726 |
| 3,818,765 | 6/1974 | Eriksen | 128/675 |
| 3,910,106 | 10/1975 | Brady | 73/726 |
| 3,946,724 | 3/1976 | LaBalme | 73/726 |
| 4,453,931 | 6/1984 | Pastrone | |
| 4,545,389 | 10/1985 | Schaberg et al. | 128/675 |
| 4,752,289 | 6/1988 | Balding et al. | 604/118 |

Primary Examiner—C. Fred Rosenbaum
Assistant Examiner—Kathleen A. Daley
Attorney, Agent, or Firm—Harry G. Thibault; Robert E. Wexler

[57] ABSTRACT

A pressure sensor assembly includes two spacedly positioned flexible supports which support an elongated rod, with one end of the elongated rod contacting a pressure detector section on a disposable pumping cassette; the pressure sensor assembly can detect pressures in the cassette both above and below atmospheric (i.e., zero psig); when pressure changes in the cassette, the pressure detection section causes axial movement of the rod and the rod, in turn, flexes the two flexible supports. Position detection means associated with one of the two supports monitors the flexural movement of the one support, providing an indication of the pressure within the cassette.

9 Claims, 4 Drawing Sheets

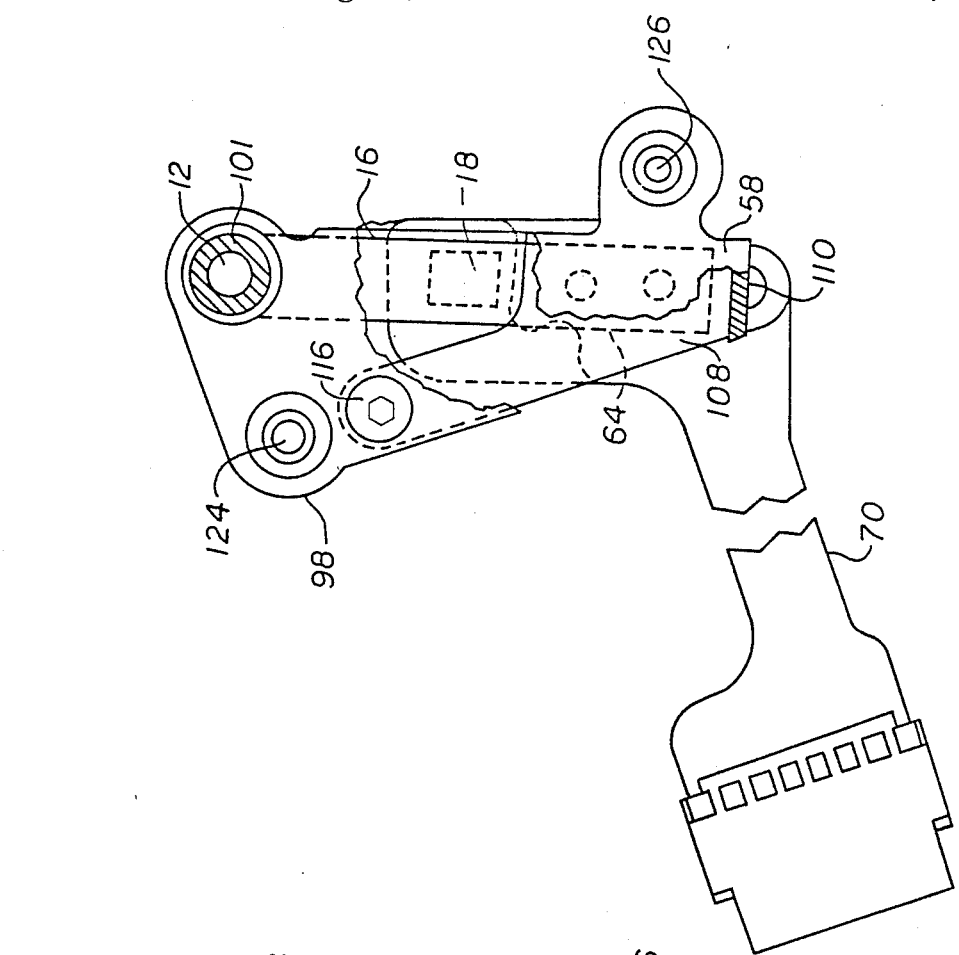
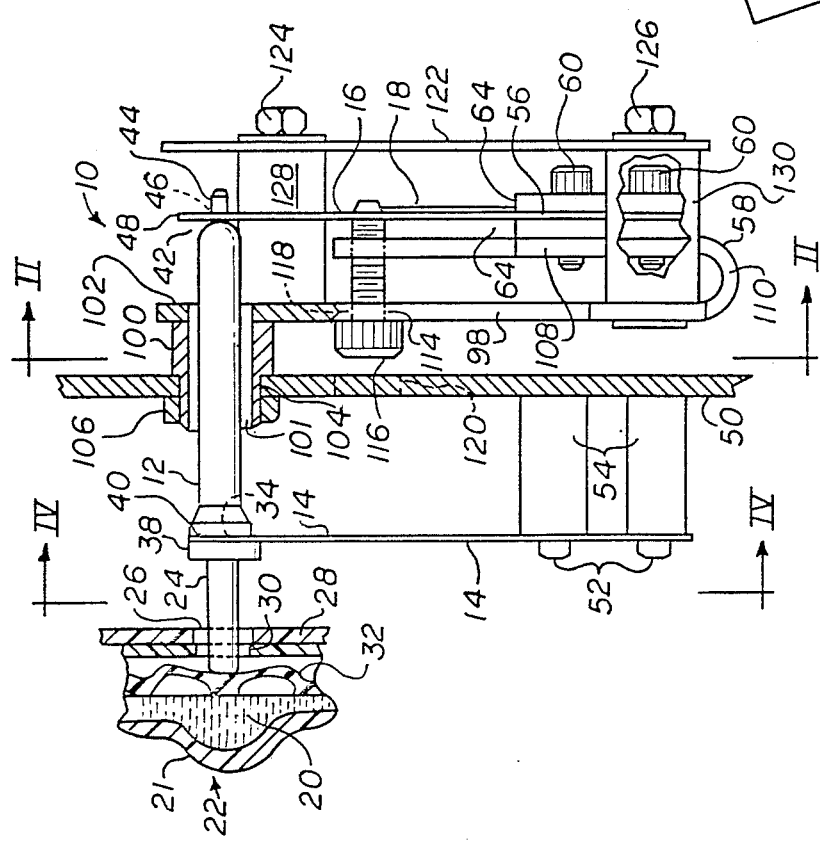
FIG. 2
FIG. 1

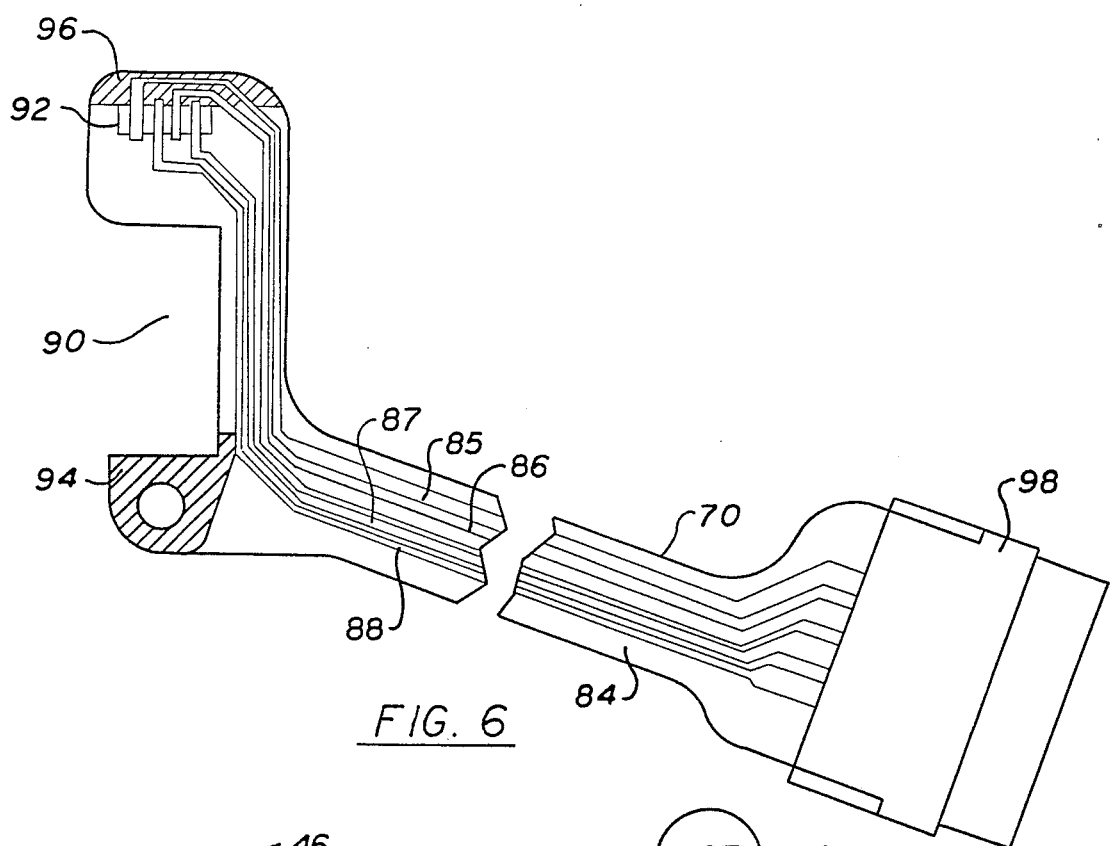
FIG. 6
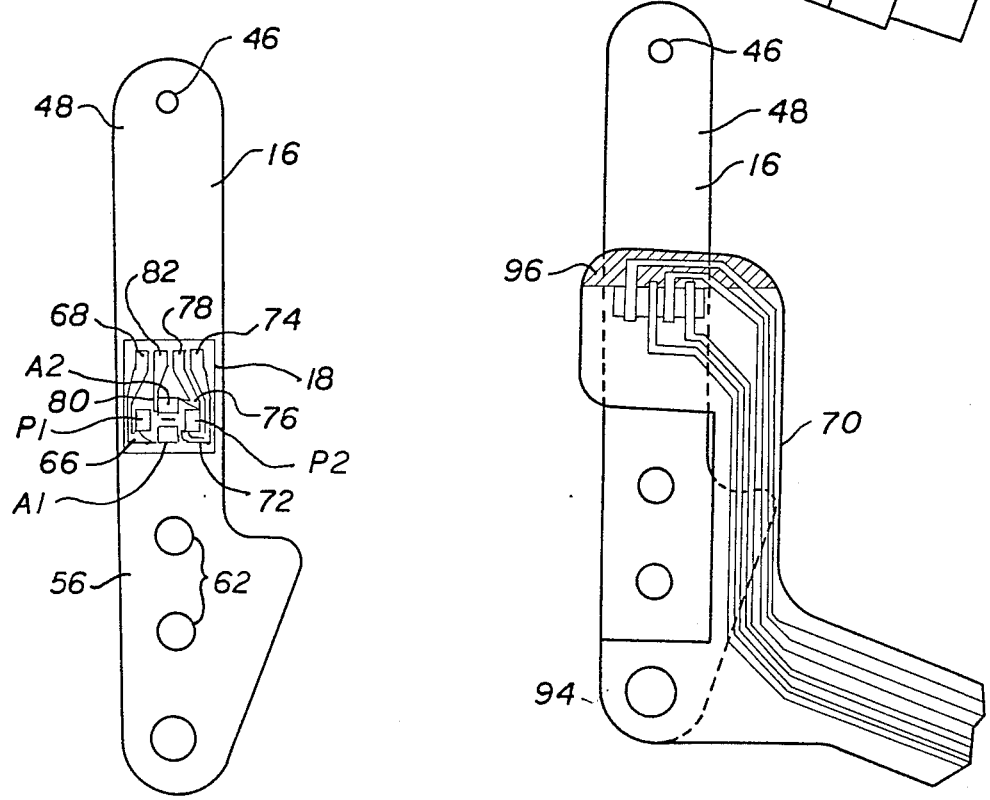
FIG. 5
FIG. 7

PRESSURE SENSOR ASSEMBLY FOR DISPOSABLE PUMP CASSETTE

BACKGROUND OF THE INVENTION

The present invention relates to pressure monitoring devices for externally monitoring the pressure within a disposable pumping cassette used to pump intravenous fluids.

In administering intravenous fluids to patients, it is becoming increasingly common to use inexpensive disposable pumping cassettes made of plastics, which are operated by non disposable driver mechanisms external to the cassette. Such systems have replaced the time honored gravity flow fluid administration systems to a large extent due to their greater accuracy and labor saving features.

Monitoring the pressure of the fluid being discharged from the cassette can provide useful information. As disclosed in U.S. Pat. No. 4,457,753, monitoring discharge pressure permits the detection of occlusions or plugged filters in the cassette outlet line leading to the patient. As disclosed in copending U.S. application Ser. No. 045,958 entitled Disposable Fluid Infusion Pumping Chamber Cassette and Drive Mechanism thereby John Pastrone (the disclosure of which is incorporated herein by reference), monitoring discharge pressure also permits the cassette and its valves to be checked for leakage. Also, the patient's blood pressure can be followed by monitoring discharge line pressure at certain times during the cassette pumping cycle as disclosed in the aforementioned patient application.

However, there should also be a pressure transducer which can detect occlusions in the cassette inlet line from the solution container to the cassette. Furthermore, there is a need for pressure transducers which can make the pressure measurements described above accurately.

SUMMARY OF THE INVENTION

The present invention is a pressure sensor assembly which includes two spacedly positioned flexible supports which support an elongated rod. One end of the elongated rod is for contacting a pressure detector section on a disposable pumping cassette. When pressure changes in the cassette, the pressure detection section causes axial movement of the rod. The rod, in turn, flexes the two flexible supports. Position detection means associated with one of the two support monitors the flexural movement of the one support, providing an indication of the pressure within the cassette. Other features of the invention will be discussed in detail below.

The pressure sensor assembly of the present invention can detect pressures in the cassette both above and below atmospheric (i.e., zero psig). Thus, occlusions in both the inlet and outlet lines to and from the cassette can be detected. Furthermore, the assembly affords accurate measurement of pressure in the cassette.

BRIEF DESCRIPTION OF THE DRAWINGS

FIG. 1 is a detailed side elevational view partially broken of the pressure detection assembly of the present invention;

FIG. 2 is a partially broken cross-sectional view taken along the plane of line II—II of FIG. 1;

FIG. 5 is a plan view of a strain gauge beam of the pressure detection assembly;

FIG. 6 is a plan view of a wiring harness used to connect the strain gauge in the strain gauge beam circuitry used in the present invention;

FIG. 7 is a plan view of the strain gauge/wiring harness assembly of the present invention.

DETAILED DESCRIPTION OF THE PREFERRED EMBODIMENT

Figure 4:
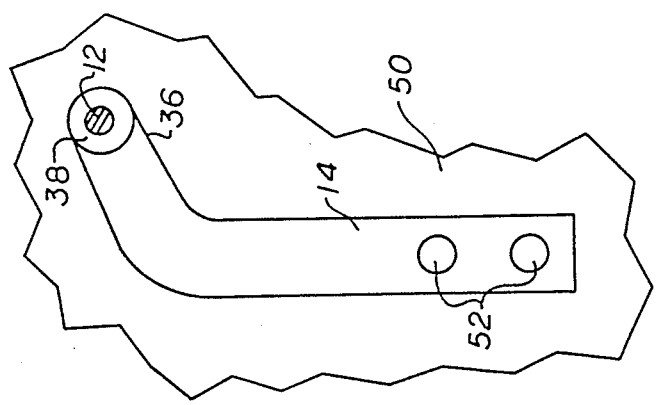
FIG. 4 is a cross sectional view taken along the plane of line IV—IV of FIG. 1.
Figure 3:
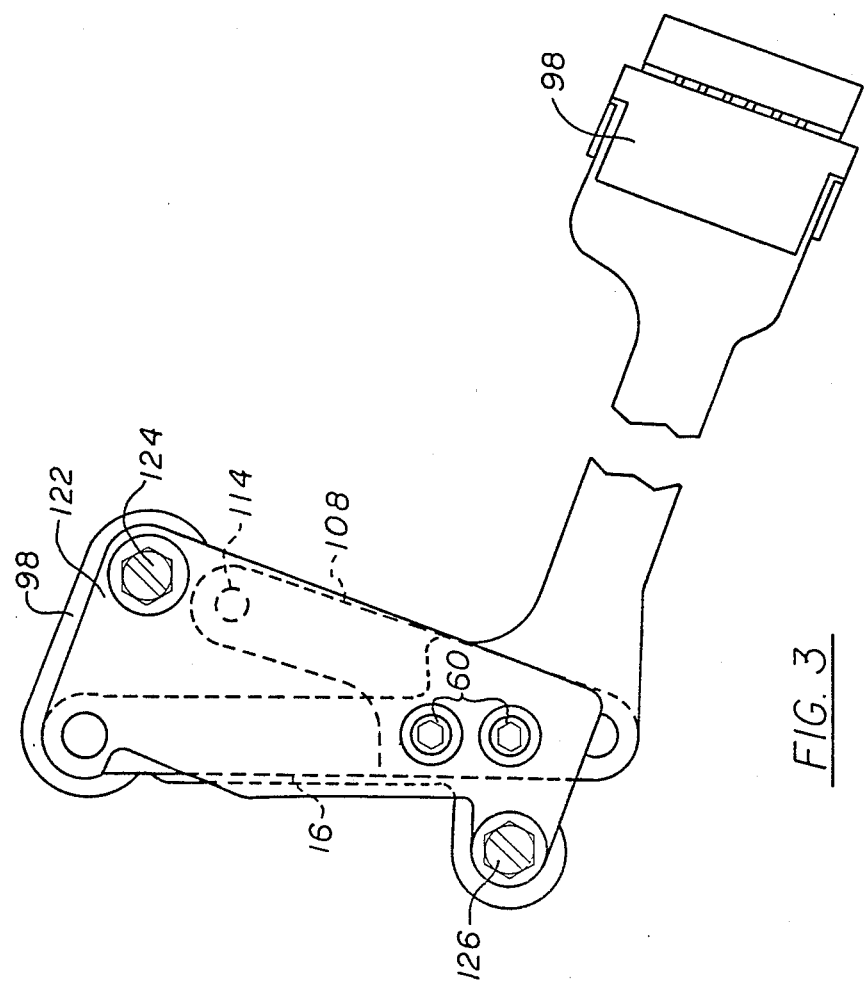
FIG. 3 is a rear elevational view of the pressure detection assembly of the present invention generally from the right hand side of FIG. 1.

The pressure detection assembly 10 of the present invention (FIGS. 1-4) includes an elongated rod or stem 12 which is supported by two spaced flexible supports: guide leaf 14 and strain gauge beam 16. A strain gauge 18 is mounted on one side of strain gauge beam 16 for detection of the flexural movement of beam 16 in response to axial movement of stem 12 caused by changes in the pressure of liquid 20 within a pumping cassette 22 which is only partially shown. A detailed description of cassette 22 is provided in U.S. patent application Ser. No. 045,958 entitled Disposable Fluid Infusion Pumping Chamber Cassette and Drive Mechanism incorporated herein by reference. As will be explained below, pressure detection assembly 10 can detect accurately both positive and negative pressures in cassette 22.

Stem 12 is an elongated rod which has narrow diameter first end 24 which extends through an opening 26 in the front panel 28 of the cassette driver of which pressure detector assembly 10 is a part. When a cassette 22 is placed in the driver, it lies flat against panel 28. First end 24 of stem 12 extends through an opening 30 in the cassette, and abuts against a resilient diaphragm 32. Diaphragm 32 expands or contracts due to changes in pressure of liquid 20. This imparts an axial movement to stem 12.

The narrow diameter first end 12 is supported within an opening 34 in the distal end 36 of guide leaf 14. A collar 38 (FIGS. 1 and 4) is press fit onto first end 24 and retains distal end 36 of guide leaf 14 against the shoulder 40 formed between first end 24 and the body of stem 12.

The second end 42 of stem 12 is rounded with a narrow diameter projection 44 extending axially from it. Projection 44 fits slideably within an opening 46 (FIGS. 1, 5 and 7) at the distal end 48 of strain gauge beam 16. Thus, stem 12 and beam 16 can exert pressure on each other, but not tension. Tension would pull them apart.

Guide leaf 14 (FIGS. 1 and 4) is a thin strip of flexible hardened steel with its distal end 36 canted with respect to the longitudinal axis of its main body. Distal end 36 supports stem 12 in the manner described above. The proximal end of leaf 14 is fixed to the chassis 50 of the cassette driver by screws 52 and spacers 54. Guide leaf 14 flexes to permit stem 12 to move horizontally as the pressure within cassette 22 changes. As stem 12 moves, guide leaf 14 flexes about its proximal end.

Strain gauge beam 16 also is formed from a thin strip of flexible hardened steel. Distal end 48 of beam 16 has an opening 46 in which projection 44 of stem 12 is slideably carried. The proximal end 56 of beam 16 is secured to a U shaped (FIG. 1) bracket 58 by fasteners 60

(FIGS. 1 and 3) which pass through openings 62 (FIG. 5) in beam 16. Beam 16 is sandwiched between spacers 64 (FIGS. 1 and 2) through which fasteners 60 pass to secure beam 16 to bracket 58.

Strain gauge 18 is adhered securely to the rear face of beam 16 intermediate the ends of the beam. Strain gauge 18 is a printed circuit Wheatstone bridge, with four resistors $A_1$, $A_2$, $P_1$ and $P_2$. A printed circuit (PC) portion 66 (FIG. 5) creates an electrical contact between resistors $A_1$ and $P_1$. PC portion 66 includes a contact pad or point 68 to which a wiring harness 70 (FIGS. 2, 6 and 7) can establish contact in a manner described below:

A printed circuit portion 72 creates an electrical contact between resistors $A_1$ and $P_2$. Printed circuit portion 72 includes a contact pad 74 which wiring harness 70 contacts. A printed circuit portion 76 creates electrical contact between resistors $P_2$ and $A_2$, and has a contact pad 78. Printed circuit portion 80 completes the bridge between resistors $A_2$ and $P_1$, and includes a contact pad 82.

Wiring harness 70 (FIGS. 6 and 7) includes a thin, flexible plastic substrate 84 on which four copper conductors 85, 86, 87 and 88 are laminated. Substrate 84 is recessed at 90 to accommodate spacers 64. Above recess 90 is a rectangular opening 92 across which solder coated portions of conductors 85 88 extend. Substrate 84 has two areas 94 and 96 coated with a contact adhesive. Areas 94 and 96 are protected prior to assembly with peel away strips (not shown). Wiring harness further includes an electrical connector 98 at its distal end to connect harness 70 to a printed circuit board containing the rest of the circuitry described below.

To assemble wiring harness 70 and strain gauge beam 16, the peel away strips covering adhesive areas 94 and 96 are removed. The wiring harness is placed on beam 16 such that opening 92 is centered over contact pads 68, 74, 78 and 82. Specifically, the solder coated portions of conductors 85, 86, 87 and 88 are centered over contact pads 68, 78, 74 and 82, respectively. Then, the wiring harness is adhered to beam 16 by adhesive areas 94 and 96 to hold the two parts in this position. Finally, heat is applied to melt the solder to adhere conductors 85, 86, 87 and 88 to pads 68, 78, 74 and 87, respectively. With the wiring harness and beam assembled, the beam can be fastened to bracket 58 as described above.

Bracket 58 is generally U shaped when viewed from the side (FIG. 1). One arm 98 is a large plate which is fixedly mounted at its distal end to chassis 50 by an externally threaded bushing 100. Bushing 100 has an axial passage 101 which is centered over an opening 102 in the distal end of arm 98. Bushing 100 is riveted to arm 98. Bushing 100 passes through an opening 104 in chassis 50, and secured to chassis 50 by a threaded collar 106. Stem 12 passes through opening 102 and passage 101 and is suspended by leaf 14 and beam 16 without contacting either bushing 100 or arm 98.

The proximal end of first arm 98 is joined to the proximal end of second arm 108 by a bight portion 110. The distal end 112 of second arm 108 is canted with respect to the vertically oriented beam 16. A threaded opening 114 extends through distal end 112. An adjustment screw 116 extends through an opening 118 (FIG. 1) in arm 98, and threads into opening 114. Adjustment screw 116 is used to adjust the distance between arms 98 and 108. Together with bracket 58, screw 116 forms an adjustable mount which is used to adjust the position of beam 16. Since beam 16 is mounted on arm 108, and arm 98 is mounted on chassis 50, the position of beam 16 relative to chassis 50 can be adjusted with screw 116. Adjustment of screw 116 allows detection of negative pressures and occlusions in the inlet line leading to the cassette. This adjustment is described below. An access opening 120 (FIG. 1) in chassis 50 is provided to permit access to screw 116 through chassis 50.

A back plate 122 is spacedly positioned from and secured to arm 98 by screws 124 and 126 and spacers 178 and 130. Back plate 122 protects beam 16.

Figure 8:
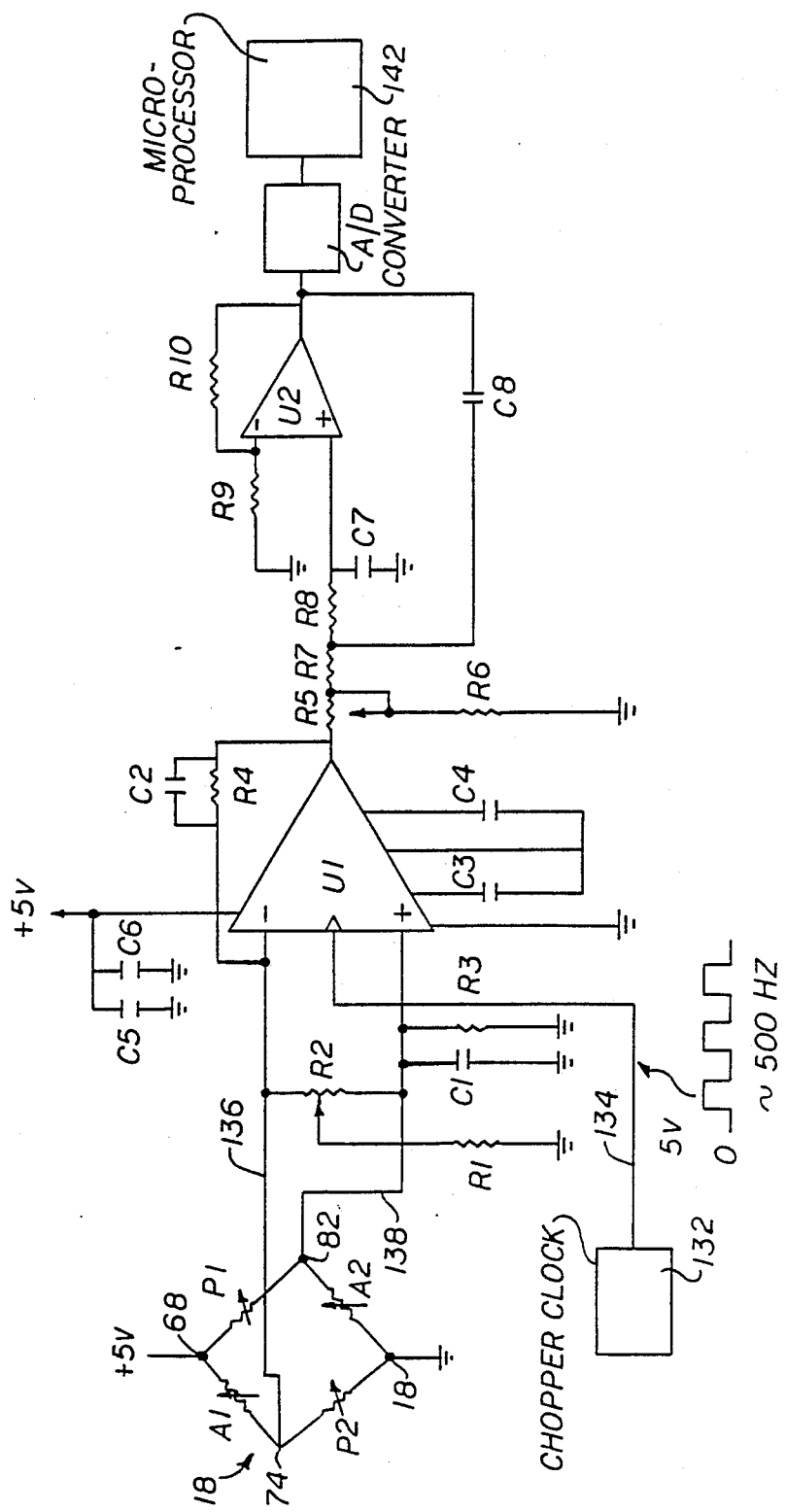
FIG. 8 is a schematic of the pressure amplifier circuitry of the present invention.

The pressure amplifier circuit is shown schematically in FIG. 8. Strain gauge 18 includes a full Wheatstone bridge with two active $A_1$, $A_2$ and two Poisson $P_1$ and $P_2$ resistive strain gauges. Contact point 68 is connected to a 5 V DC source. Contact point 78 is grounded. Contact points 74 and 82 are connected to differential amplifier $U_1$, a ICL7652 amplifier sold by Intersil. Amplifier $U_1$ with capacitors $C_3$ and $C_4$ from a chopper stabilized CMOS differential amplifier with an external chopping clock 132 operating at about 500 Hz, connected to amplifier $U_1$ by line 134. Chopper clock 132 provides an operating square wave signal of 5 volts at 500 Hz to amplifier $U_1$.

A variable resistor $R_2$ is connected across the output lines 136 and 138 from the Wheatstone bridge. $R_2$ with resistor $R_1$ is used to adjust the zero (or offset) of the bridge output voltage. The reason for this adjustment of resistor R is described below.

Lines 136 and 138 are connected to the inputs of amplifier $U_1$. The gain of the $U_1$ amplifier circuit is determined by the resistance of the strain gauge bridge (350 ohms nominal), and of a feedback resistor $R_4$. Variable resistor $R_5$ and resistor $R_6$ allow factory calibration of the overall gain of the $U_1$ amplifier circuit The adjustment of resistor $R_5$ will be explained below:

Capacitor $C_1$ and $C_2$, together with resistors $R_3$ and $R_4$, form a low pass filter at about 200 Hz to reduce noise at the output of amplifier $U_1$. Capacitors $C_5$ and $C_6$ are power supply (+5 V) decoupling capacitors.

Amplifier $U_2$ is an LM 358 amplifier sold by National Semiconductor. Amplifier $U_2$ with resistors $R_7$, $R_8$, $R_9$ and $R_{10}$ and capacitors $C_7$ and $C_8$ form a low pass Bessel filter to reduce noise in the signal and to keep the signal spectrum within the limits set by analog/digital converter 140 to which the output of amplifier $U_2$ is applied. The output signal of A/D converter 140 is applied to the input of a microprocessor 142 which controls the cassette driver.

Before use, the pressure detection assembly must be mechanically and electrically calibrated properly so that it is accurate and can detect positive and negative pressures. To detect a negative pressure (i.e., an occlusion in the fluid line leading to the cassette), stem 12 must be able to move inwardly of the cassette (i.e., to the left in FIG. 1). A negative pressure in cassette 22 will cause diaphragm 32 to retract inwardly. Thus, stem 12 must be able to follow this inward movement for pressure detector assembly 10 to detect a negative pressure.

To calibrate pressure detection assembly 10 to detect a negative pressure, cassette 22 is removed from the driver. Adjustment screw 116 is adjusted to bias beam 16 against end 42 of stem 12 to force end 24 of stem 12 outward of panel 28 (i.e., to urge stem 12 to the left in FIG. 1 . Screw 116 is adjusted to move end 24 of stem 12 sufficiently outward to allow stem 12 to travel inward of a cassette if a negative pressure draws diaphragm 32 inward.

Of course, when a cassette is placed in the driver, as shown in FIG. 1, the resilience of diaphragm 32 and pressure of the liquid in the cassette will force end 24 of stem 12 inward into panel 28 (i.e., force stem 12 to the right in FIG. 1). Variable resistor $R_2$ is adjusted so that when the liquid in a cassette 22 is at atmospheric pressure (i.e., zero psig), the output voltage of the bridge (i.e., the input voltage of amplifier $U_1$) is zero.

With resistor $R_2$ and screw 116 so adjusted, strain gauge 18 and amplifier $U_1$ can detect both positive pressures (i.e., when diaphragm 32 urges stem 12 to the right in FIG. 1) and negative pressures (i.e., when diaphragm 32 is drawn inward of the cassette and beam 16 urges stem 12 to the left in FIG. 1).

Resistor $R_5$ is adjusted to control the overall gain of the circuit. The gain should be adjusted so the pressure displayed by microprocessor 142 is the same pressure as that in the cassette. Resistors $R_5$ and $R_2$ interact so that the gain and offset adjustments have to be made iteratively, adjusting $R_2$, then $R_5$ and repeating the process until both offset and gain are at their desired values.

With the assembly and calibration of the pressure detector described, its operation can easily be understood. As disclosed in U.S. patent application Ser. No. 045,958 entitled Disposable Fluid Infusion Pumping Cassette and Drive Mechanism. Therefore, cassette 22 includes a pumping chamber having an elastomeric diaphragm over it, and inlet and outlet valves controlling the flow of fluid into and out of the pumping chamber. The pumping chamber is operated by a plunger (which is part of the driver) which reciprocates against the diaphragm. The inlet valve communicates with a line leading to a container of fluid to be infused. The pumping chamber outlet valve is upstream of the pressure detection chamber 21 shown in FIG. 1. The pressure detection chamber has diaphragm 32 disposed across it.

Negative pressure situations occur if there is an occlusion in the inlet line from the container to the cassette. When the inlet line is occluded, the pumping chamber diaphragm (which has been urged inwardly into the pumping chamber by the plunger on a previous fluid delivery stroke) cannot draw fluid through the opened inlet valve (the outlet valve being closed) when the plunger is retracted. When the plunger is retracted, the pumping chamber diaphragm simply remains depressed inward and cannot retract to its normal condition and draw liquid into the pumping chamber. Thus, the pressure on the pumping chamber is below zero psig, i.e. a negative pressure.

On the succeeding fluid delivery stroke, the inlet valve closes and the outlet valve opens, (simultaneously, the plunger is urged into the cassette pumping chamber with little or no pumping action). With the outlet valve open, the pressure detector chamber 21 is exposed to the negative pressure in the pumping chamber. There is a momentary drop in pressure in chamber 21 before the pressure on the pumping chamber rises to the pressure in the line leading the the patient. This pressure drop will be detected by stem 12 because diaphragm 32 will be drawn inwardly of the cassette.

If there is an occlusion in the line leading to the patient, there will be a dramatic increase in pressure when the plunger tries to pump fluid from the pumping chamber. The pressure increase will be detected when diaphragm 32 forces stem 12 against beam 16.

The pressure detection assembly can also be used to check the integrity of the pumping chamber inlet and outlet valves. After the pumping chamber is filled with liquid, the pumping chamber inlet and outlet valves are closed. The pumping chamber is then pressurized by the plunger and held pressurized for a brief period of time. If the valves are leaky, a certain amount of liquid will leak from the pumping chamber during the "hold" period. After the hold period, the pumping chamber outlet valve is opened. The pressurized fluid will cause a pressure surge or "spike" in chamber 22 downstream of the pumping chamber outlet valve. If fluid leaked in the hold period, the spike will be of a lower magnitude than if fluid did not leak. The spike is detected by pressure detector assembly 10. If it is unacceptably low, microprocessor 142 will alert the user to reject the cassette.

Finally, as described in the aforesaid patent application, the patient's blood pressure can be monitored through cassette 22. During the fluid pumping chamber refill stroke of the fluid pump chamber plunger, the pumping chamber outlet valve is closed. Thus, the pressure of liquid in pressure detection chamber 21 is the same as the patient's blood pressure, the cassette being connected by a tube to a needle in the patient, typically. Patient blood pressure data can be taken by microprocessor 142 during refill strokes. If blood pressure changes unduly, microprocessor will alert nursing personnel by sounding an alarm. Real time display of patient blood pressure can also be provided.

While one embodiment of the invention has been shown, other embodiments will become apparent to others skilled in the art. These additional embodiments are included within the scope of the claims which follow unless their terms explicitly state otherwise.

We claim:

1. A driver mechanism for driving a disposable pumping cassette with a pressure detection section, comprising:
    an elongated rod member with a first end in contact with the cassette pressure detection section, said rod member adapted to move in response to a change in pressure in the cassette;
    a first flexible support with said first end of said elongated rod being supported by a first end of said first support, a second end of said first support being fixedly mounted in said driver mechanism whereby said first end of said first support flexes in response to movement of said rod;
    a second flexible support with a second end of said elongated rod being supported by a first end of said second support;
    a second end of said second support being mounted on an adjustable mounting means whereby said first end of said second support flexes in response to movement of said rod; and
    position detection means associated with one of said first or second supports for monitoring flexural movement of said one support;
    whereby the pressure in the cassette can be monitored by monitoring said position detection means.

2. The driver mechanism as recited in claim 1, wherein said position detection means is associated with said second flexible support.

3. The driver mechanism as recited in claim 2, wherein said position detection means includes a strain gauge mounted on said second support.

4. The driver mechanism as recited in claim 3, wherein said second rod member includes a rounded shoulder with an axial projection at its other end, and said second support includes an opening which receives said projection.

5. The driver mechanism as recited in claim 3, wherein said rod member and said second support are interconnected so as to exert a compression force on each other at their connection but not a tension force.

6. The driver mechanism as recited in claim 3, wherein said strain gauge includes a Wheatstone bridge.

7. The driver mechanism as recited in claim 6, further including a differential amplifier connected across said bridge, a voltage source across said bridge, and offset adjustment means for adjusting the output voltage of said bridge.

8. The driver mechanism as recited in claim 1, wherein said adjustable mounting means includes a U-shaped bracket, one arm of said U being fixedly secured to said driver mechanism, said second support being mounted on the other arm of said U, and means for adjusting the distance between the two arms of said U shaped bracket.

9. The driver mechanism as recited in claim 6, wherein said adjustment means includes a threaded member extending between the arms of said U-shaped bracket.

* * * * *